United States Patent
Lin et al.

(10) Patent No.: US 9,518,251 B2
(45) Date of Patent: *Dec. 13, 2016

(54) METHOD FOR ENHANCING THERAPEUTIC EFFECT OF STEM CELLS ON AUTOIMMUNE DISEASES, CARDIOVASCULAR DISEASES, AND/OR HEMATOLOGICAL DISEASES

(71) Applicant: GWO XI STEM CELL APPLIED TECHNOLOGY CO., LTD., Zhubei, Hsinchu County (TW)

(72) Inventors: Shinn-Zong Lin, Zhubei (TW); Horng-Jyh Harn, Zhubei (TW); Ru-Huei Fu, Zhubei (TW); Shih-Ping Liu, Zhubei (TW); Po-Cheng Lin, Zhubei (TW); Ming-Hsi Chuang, Zhubei (TW)

(73) Assignee: GWO XI STEM CELL APPLIED TECHNOLOGY CO., LTD., Zhubei, Hsinchu County (TW)

( * ) Notice: Subject to any disclaimer, the term of this patent is extended or adjusted under 35 U.S.C. 154(b) by 0 days.

This patent is subject to a terminal disclaimer.

(21) Appl. No.: 15/074,490

(22) Filed: Mar. 18, 2016

(65) Prior Publication Data

US 2016/0208217 A1 Jul. 21, 2016

Related U.S. Application Data

(62) Division of application No. 14/821,309, filed on Aug. 7, 2015, which is a division of application No. 14/552,014, filed on Nov. 24, 2014.

(30) Foreign Application Priority Data

Sep. 17, 2014 (TW) .............................. 103132044 A

(51) Int. Cl.
| | |
|---|---|
| *C12N 5/00* | (2006.01) |
| *C12N 5/02* | (2006.01) |
| *C12N 5/0775* | (2010.01) |
| *A61K 35/545* | (2015.01) |
| *A61K 35/28* | (2015.01) |

(52) U.S. Cl.
CPC ............. *C12N 5/0667* (2013.01); *A61K 35/28* (2013.01); *A61K 35/545* (2013.01); *C12N 2501/40* (2013.01)

(58) Field of Classification Search
None
See application file for complete search history.

(56) References Cited

U.S. PATENT DOCUMENTS

| | | |
|---|---|---|
| 2005/0239897 A1 | 10/2005 | Pittenger et al. |
| 2009/0192218 A1* | 7/2009 | D'Orazio ............ A61K 31/343 514/470 |
| 2011/0177106 A1 | 7/2011 | Lau | |

FOREIGN PATENT DOCUMENTS

| | | |
|---|---|---|
| CN | 102397272 | 4/2012 |
| CN | 104042606 | 9/2014 |
| TW | 201434465 | 9/2014 |

OTHER PUBLICATIONS

Zeng et al (Bioorg. Medic. Chem., 16:5109-5114 (2008).*
Elabd et al (Stem Cells, 27:2753-2760 (2009).*
Hing-Lok et al., Chin. J. Integr. Med., 18(12):903-908 (2012).*
Kuang et al (Brain Res., 1102:145-153 (2006).*
Lee et al., J. Ethnopharm., 139:739-745 (2012).*
Tanaka et al., Neurosci., 164:1224-1234 (2009).*
Wang et al., Neural Regen. Res., 8(35): 3353-3358 (2013).*
Gunawardana et al., Diabetes, 61:674-682 (2012).*
Kang, S.K. et al., "Journal of Mesenchymal Stem Cells for Homing: Strategies to Enhance Efficacy and Safety of Stem Cell Therapy", Stem Cells International, vol. 2012, Article ID 342968, 2012, 11 pages.
Reagan, M.R., et al., "Concise Review: Mesenchymal Stem Cell Tumor-Homing: Detection Methods in Disease Model Systems", Stem Cells, vol. 26(6), 201, pp. 920-927.
Ding, D.C. et al., "Enhancement of neuroplasticity through upregulation of β1-integrin in human umbillical cord-derived stromal cell implanted stroke model", Neurobiology of Disease, vol. 27, Issue 3, Sep. 2007, pp. 339-353.
Sutton, M.T. et al., "Stem Cells: Innovations in Clinical Applications", Stem Cells International, vol. 2014, Article ID 516278, 2014, 9 pages.
Bliss, T.M. et al., "Optimizing the success of cell transplantation therapy for stroke", Neurobiology of Disease, vol. 37, Issue 2, Feb. 2010, pp. 275-283.
File History of U.S. Appl. No. 14/552,014, filed Nov. 24, 2014.
File History of U.S. Appl. No. 14/821,309, filed Aug. 7, 2015.
Peng, Hai-Yan, et al., "Neuroprotective Effect of Z-Ligustilide Against Permanent Focal Ischemic Damage in Rats," Biol. Pharm. Bull., vol. 30(2), Feb. 2007, pp. 309-312.
Zeng, He-Ping, et al., "Characterization of Chemical Components in Extracts from Si-wu Decoction with Proliferation-Promoting Effects on Rat Mesenchymal Stem Cells," Bioorganic & Medicinal Chemistry, vol. 16, Mar. 2008, pp. 5109-5114.
Kuang, X., et al., "Neuroprotective Role of Z-Ligustilide Against Forebrain Ischemic Injury in ICR Mice," Brain Research, vol. 1102, 2006, pp. 145-153.

* cited by examiner

*Primary Examiner* — Thomas J Visone
(74) *Attorney, Agent, or Firm* — Ping Wang; Andrews Kurth LLP

(57) ABSTRACT

A method for enhancing the therapeutic effect of stem cells on autoimmune diseases, cardiovascular diseases, and/or hematological diseases is provided. The method comprises pre-treating the stem cells with ligustilide to increase the expression of differentiation-promoting genes in the stem cells, increase the expression of homing-promoting genes in the stem cells, and/or decrease the expression of inflammatory genes in the stem cells, wherein the treatment is conducted in a culture medium of the stem cell.

16 Claims, 5 Drawing Sheets

(4 of 5 Drawing Sheet(s) Filed in Color)

SEQUENCE LISTING

```
<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: BDNF primer- Forward Sequence

<400> SEQUENCE: 1
gagctgagcg tgtgtgacag                                          20

<210> SEQ ID NO 2
<211> LENGTH: 20
<212> TYPE: DNA
<213> ORGANISM: Artificial Sequence
<220> FEATURE:
<223> OTHER INFORMATION: BDNF primer-  Reverse Sequence

<400> SEQUENCE: 2
actgggtagt tcggcactgg                                          20

<210> SEQ ID NO 3
<211> LENGTH: 20
<212> TYPE: DNA
<213> ORGANISM: Artificial Sequence
<220> FEATURE:
<223> OTHER INFORMATION: NURR1 primer- Forward Sequence

<400> SEQUENCE: 3
cgcacatgat cgagcagagg                                          20

<210> SEQ ID NO 4
<211> LENGTH: 20
<212> TYPE: DNA
<213> ORGANISM: Artificial Sequence
<220> FEATURE:
<223> OTHER INFORMATION: NURR1 primer-  Reverse Sequence

<400> SEQUENCE: 4
attccggcga cgcttgtcca                                          20

<210> SEQ ID NO 5
<211> LENGTH: 20
<212> TYPE: DNA
<213> ORGANISM: Artificial Sequence
```

-continued

<220> FEATURE:
<223> OTHER INFORMATION: CXCR4 primer- Forward Sequence

<400> SEQUENCE: 5
ggccttcatc agtctggacc					20

<210> SEQ ID NO 6
<211> LENGTH: 20
<212> TYPE: DNA
<213> ORGANISM: Artificial Sequence
<220> FEATURE:
<223> OTHER INFORMATION: CXCR4 primer-  Reverse Sequence

<400> SEQUENCE: 6
agtaaggcag ccaacaggcg					20

<210> SEQ ID NO 7
<211> LENGTH: 21
<212> TYPE: DNA
<213> ORGANISM: Artificial Sequence
<220> FEATURE:
<223> OTHER INFORMATION: SDF1 primer- Forward Sequence

<400> SEQUENCE: 7
atgaacgcca aggtcgtggt c					21

<210> SEQ ID NO 8
<211> LENGTH: 26
<212> TYPE: DNA
<213> ORGANISM: Artificial Sequence
<220> FEATURE:
<223> OTHER INFORMATION: SDF1 primer-  Reverse Sequence

<400> SEQUENCE: 8
cttgtttaaa gctttctcca ggtact				26

<210> SEQ ID NO 9
<211> LENGTH: 20
<212> TYPE: DNA
<213> ORGANISM: Artificial Sequence
<220> FEATURE:
<223> OTHER INFORMATION: IL-6 primer- Forward Sequence

<400> SEQUENCE: 9
tgccagcctg ctgacgaagc					20

<210> SEQ ID NO 10
<211> LENGTH: 20
<212> TYPE: DNA
<213> ORGANISM: Artificial Sequence
<220> FEATURE:
<223> OTHER INFORMATION: IL-6 primer-  Reverse Sequence

<400> SEQUENCE: 10
tctgtgccca gtggacaggt					20

<210> SEQ ID NO 11
<211> LENGTH: 20
<212> TYPE: DNA
<213> ORGANISM: Artificial Sequence
<220> FEATURE:
<223> OTHER INFORMATION: IL-8 primer- Forward Sequence

<400> SEQUENCE: 11
gctggccgtg gctctcttgg					20

```
<210> SEQ ID NO 12
<211> LENGTH: 20
<212> TYPE: DNA
<213> ORGANISM: Artificial Sequence
<220> FEATURE:
<223> OTHER INFORMATION: IL-8 primer- Reverse Sequence

<400> SEQUENCE: 12
tccacaaccc tctgcaccca                                               20

<210> SEQ ID NO 13
<211> LENGTH: 23
<212> TYPE: DNA
<213> ORGANISM: Artificial Sequence
<220> FEATURE:
<223> OTHER INFORMATION: GAPDH primer- Forward Sequence

<400> SEQUENCE: 13
ggagccaaac gggtcatcat ctc                                           23

<210> SEQ ID NO 14
<211> LENGTH: 22
<212> TYPE: DNA
<213> ORGANISM: Artificial Sequence
<220> FEATURE:
<223> OTHER INFORMATION: GAPDH primer- Reverse Sequence

<400> SEQUENCE: 14
gaggggccat ccacagtctt ct                                            22
```

METHOD FOR ENHANCING THERAPEUTIC EFFECT OF STEM CELLS ON AUTOIMMUNE DISEASES, CARDIOVASCULAR DISEASES, AND/OR HEMATOLOGICAL DISEASES

This application is a Division of U.S. application Ser. No. 14/821,309, filed Aug. 7, 2015, which is a Division of U.S. application Ser. No. 14/552,014, filed Nov. 24, 2014, which claims priority to Taiwan Patent Application No. 103132044 filed on Sep. 17, 2014, in the Taiwan Intellectual Property Office, the disclosure of which is incorporated herein in its entirety by reference.

BACKGROUND OF THE INVENTION

1. Field

The present invention relates to the use of ligustilide, especially to the use of ligustilide in stem cell treatment, in particular the use of ligustilide in stem cell treatment of a stroke. The therapeutic effect of the stem cells can be enhanced by treating the stem cells with ligustilide. In particular, the treatment of ligustilide can increase the expression of differentiation-promoting genes in the stem cells, increase the expression of homing-promoting genes in the stem cells, and/or decrease the expression of inflammatory genes in the stem cells. In addition, the present invention also relates to a combined use of ligustilide and ligustilide-treated stem cells, which provides a more efficient therapeutic effect of stem cell treatment.

2. Descriptions of the Related Art

Stem cells, depending on their abilities to self-renew and to differentiate, can be classified into the following four types: totipotent stem cells, pluripotent stem cells, multipotent stem cells and unipotent stem cells. Depending on the appearance order during the developmental process and distributional profile of stem cells, stem cells can be classified into the following two types: embryonic stem cells (ES cells) and adult stem cells. In addition, researchers have shown that cell differentiation is reversible. By introducing specific genes into fully differentiated matured somatic cells, the matured somatic cells are induced to reprogram and form pluripotent cells with characteristics and functions similar to those of an embryonic stem cell, i.e., to form induced pluripotent stem cells (iPS cells). These induced pluripotent stem cells can differentiate into tissues of the human body, and thus, can be used in the research and therapy of the disease.

Currently, in the field of medical research, stem cell therapy brings hope to the patients suffering from diseases which lack effective treatment, such as diabetes mellitus, autoimmune rejection, stroke, myocardial infarction, renal failure, leukemia, muscular dystrophy, severe anemia, Alzheimer's disease, Parkinson's disease, and cancer. The pluripotency of stem cells may solve the long-term predicament that is encountered in the treatment of these diseases.

For example, strokes are the most common neurological system disease. Depending on the cause, strokes can be classified as either ischemic or hemorrhagic. According to statistical data, a stroke is one of the top ten leading causes of death in the world. However, only few anti-coagulant drugs or thrombolytic agents can be used for treating strokes, and these drugs and agents are not suitable for every patients suffering from stroke. Therefore, there is an urgent necessity for a novel therapeutic method. Stem cell therapy is by far the most potential therapeutic method in clinical trials. In 1998, stem cell therapy was first applied to the treatment of strokes. Over recent years, the U.S. Food and Drug Administration (FDA) has approved the clinical use of stem cells to treat stroke patients.

Researchers have shown that stem cells indeed have a therapeutic effect on treating stroke, however, the survival rate of stem cells after being transplanted into a subject's body was unfavorable. Therefore, there is a necessity and urgency for developing a method or a drug for enhancing the therapeutic effect of stem cells effectively to improve the disease cure rate.

Inventors of the present invention found that stem cells treated with ligustilide can provide an enhanced therapeutic effect. In addition, the therapeutic effect provided by a combination of ligustilide and ligustilide-treated stem cells is better than that provided by using ligustilide-treated stem cells independently.

SUMMARY OF THE INVENTION

An objective of the present invention is to provide a method for enhancing the therapeutic effect of a stem cell, comprising treating the stem cell with ligustilide, wherein the treatment is conducted in a culture medium of the stem cell.

Another objective of the present invention is to provide a composition for enhancing the therapeutic effect of a stem cell, comprising ligustilide.

Yet another objective of the present invention is to provide a stem cell kit with an enhanced therapeutic effect, comprising a stem cell, a culture medium for the stem cell, and ligustilide. Preferably, the ligustilide comprises a first part and a second part, wherein the first part is used in combination with the culture medium to pre-treat the stem cell, and the second part is used in combination with ligustilide-treated stem cells in a stem cell therapy.

Yet another objective of the present invention is to provide a use of ligustilide in the manufacture of a medicament, wherein the medicament is used in combination with ligustilide-treated stem cells in a stem cell therapy.

Yet another objective of the present invention is to provide a method of stem cell treatment, comprising administering to a subject in need an effective amount of stem cells, wherein the stem cells have been treated with ligustilide. Preferably, the method comprising administering to the subject in need ligustilide and stem cells separately or simultaneously, wherein the stem cells have been treated with ligustilide.

The detailed technology and preferred embodiments implemented for the present invention are described in the following paragraphs accompanying the appended drawings for people skilled in this field to well appreciate the features of the claimed invention.

BRIEF DESCRIPTION OF THE DRAWINGS

The file of this patent contains at least one drawing executed in color. Copies of this patent with color drawings will be provided by the Patent and Trademark Office upon request and payment of the necessary fee.

FIG. 4A represents the time required for the mice to pass through the balance beam at different days post-treatment; and FIG. 4B represents the foot-fault score of the mice at different days post-treatment, wherein Group 1 is a non-stroke mouse without treatment (i.e., a pseudo-operation group), Group 2 is a stroke mouse administered with saline, Group 3 is a stroke mouse administered with stem cells without being treated with ligustilide, and Group 4 is a stroke mouse administered with ligustilide-treated stem cells;

FIG. 5A represents the time required for the mice to pass through the balance beam at different days post-treatment, and FIG. 5B represents the foot-fault score of the mice at different days post-treatment, wherein Group 1 is a non-stroke mouse without treatment (i.e., a pseudo-operation group), Group 2 is a stroke mouse administered with saline, Group 3 is a stroke mouse administered with stem cells without being treated with ligustilide, Group 4 is a stroke mouse administered with ligustilide-treated stem cells, Group 5 is a stroke mouse administered with ligustilide-treated stem cells and 30 mg/kg-body weight of ligustilide simultaneously; and Group 6 is a stroke mouse administered with ligustilide-treated stem cells and 90 mg/kg-body weight of ligustilide simultaneously; FIG. 6A represents the total traveled distance of the mice at different days post-treatment; and FIG. 6B represents the movement time of the mice at different days post-treatment, wherein Group 1 is a non-stroke mouse without treatment (i.e., a pseudo-operation group), Group 2 is a stroke mouse administered with saline, Group 3 is a stroke mouse administered with stem cells without being treated with ligustilide, Group 4 is a stroke mouse administered with ligustilide-treated stem cells, Group 5 is a stroke mouse administered with ligustilide-treated stem cells and 30 mg/kg-body weight of ligustilide simultaneously; and Group 6 is a stroke mouse administered with ligustilide-treated stem cells and 90 mg/kg-body weight of ligustilide simultaneously.

DESCRIPTION OF THE PREFERRED EMBODIMENT

Figure 1A:
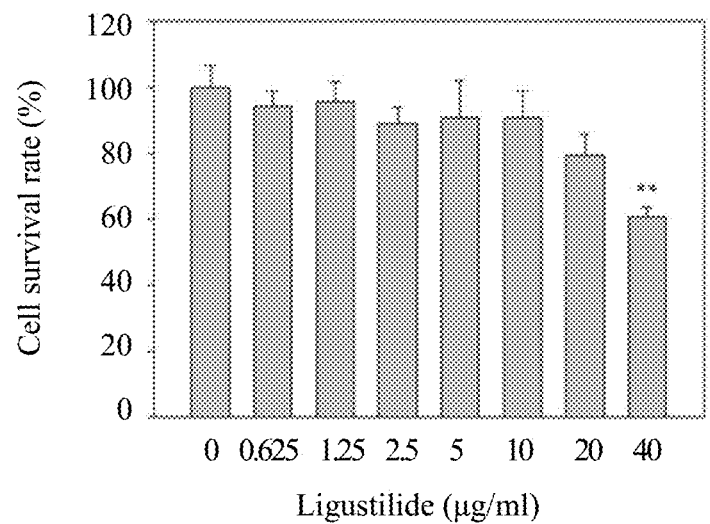
FIGS. 1A and 1B are statistical bar diagrams showing the percentages of the survival rate of adipose-derived stem cells (ADSCs) which have been treated with ligustilide for 24 or 48 hours, wherein the vertical axis represents the survival rate of the cells and the horizontal axis represents the concentration of ligustilide.

The following will describe some embodiments of the present invention in detail. However, without departing from the spirit of the present invention, the present invention may be embodied in various embodiments and should not be limited to the embodiments described in the specification. In addition, unless otherwise indicated herein, the expressions "a," "the," or the like recited in the specification of the present invention (especially in the claims) are intended to include the singular and plural forms. Furthermore, the term "effective amount" or "amount effective for treatment" used in this specification refers to the amount of the compound that can at least partially alleviate the condition that is being treated in a suspected subject when administered to the subject in need. The term "subject" used in this specification refers to a mammalian, including human and non-human animals.

As well-known in the art, stem cells can be used in the application of treating autoimmune diseases (e.g., diabetes mellitus and autoimmune rejection), treating digestive diseases (e.g., anus/digestive fistula diseases), treating hepatic diseases (e.g., hepatocirrhosis and hepatic fibrosis), treating renal diseases (e.g., renal failure), treating cardiovascular diseases (e.g., stroke and myocardial infarction), treating neurological diseases (e.g., Alzheimer's disease and Parkinson's disease), treating hematological diseases (e.g., leukemia), treating bone degeneration (e.g., degenerative arthritis, degeneration of knee cartilage), treating periodontitis, treating tendonitis, treating spinal injury, treating head trauma, plastic surgery (e.g., hemifacial atrophy and sunken scar), treating alopecia, whitening skin, and/or eliminating wrinkles. The aforementioned description can be seen in, for example, "Stem cells: innovations in clinical applications. *Stem Cells int*. Volume 2014, Article ID 516278, 9 pages," which is entirely incorporated hereinto by reference.

However, the survival rate of stem cells was unfavorable after being transplanted into a subject's body. Researchers have proven that the primary cause of this phenomena is that stem cells may induce an inflammatory reaction after being transplanted into a subject's body. If the expressions of inflammatory factors in stem cells can be decreased, the inflammatory reaction induced by stems cells after being transplanted into a subject's body can be reduced. Therefore, the survival rate of stem cells will be increased and the therapeutic effect of stem cells will be enhanced. The aforementioned description can be seen in, for example, "Optimizing the success of cell transplantation therapy for stroke. *Neurobiol Dis*. 37:275-283 (2010)," which is entirely incorporated hereinto by reference.

It has also been proven that if the expressions of differentiation-promoting genes in stem cells can be increased, the differentiation of the stem cells into tissue of the body can be promoted, and thus, is favorable for the application of stem cells in treating diseases. On the other hand, if the expression of homing-promoting genes in stem cells can be increased, the stem cells will be promoted to locate into the impaired target tissue and perform its repair function to achieve the effect of treating diseases even if the stem cells are administered as an intravenous injection to the subject. The aforementioned description can be seen in, for example, "Journey of mesenchymal stem cells for homing: strategies to enhance efficacy and safety of stem cell therapy. Stem Cell Int. Volume 2012, Article ID 342968, 11 pages;" and "Concise review: Mesenchymal stem cell tumor-homing: detection methods in disease model systems. *Stem Cells*. 29(6):920-927 (2011)," which are entirely incorporated hereinto by reference.

Inventors of the present invention found that treating stem cells with ligustilide can effectively increase the expression of differentiation-promoting genes therein, increase the expression of homing-promoting genes therein, and decrease the expression of inflammatory genes therein, wherein the differentiation-promoting genes include Nuclear receptor-related factor 1 (NURR1) and brain-derived neurotrophic factor (BDNF); the homing-promoting genes include C-X-C chemokine receptor type-4 (CXCR4) and stromal cell-derived factor-1αβ (SDF1αβ); and the inflammatory genes include interleukin-6 (IL-6) and interleukin-8 (IL-8).

Researchers have further confirmed that treating stem cells with ligustilide can effectively improve the therapeutic effect of the stem cells. Therefore, the present invention relates to a discovery about enhancing the therapeutic effect of stem cells that provides a composition and a method for enhancing the therapeutic effect of stem cells. The composition comprises ligustilide, and the method comprises treating a stem cell with ligustilide in a culture medium of the stem cell. The phrase "treating the stem cell with ligustilide in a culture medium of the stem cell" used in this specification means that when conducting the treatment, the stem cells were placed in a culture medium of the stem cells.

The composition and method of the present invention can be used in any suitable stem cells and include, for example, an embryonic stem cell, an adult stem cell, and an induced pluripotent stem cell. The adult stem cells include, for example, a hematopoietic stem cell, a mesenchymal stem cell, an umbilical cord blood stem cell, a peripheral blood stem cell, a neural stem cells, an epithelial stem cell, a muscle stem cell, an adipose-derived stem cell, a pancreas stem cell, a limbal stem cell, a hepatic stem cell, and an intestinal stem cell. In one embodiment, the composition and method of the present invention are used to enhance the therapeutic effect of the adipose-derived stem cells (ADSCs), for example, the effect of treating strokes.

According to the present invention, if stem cells are pre-treated with a composition comprising ligustilide before being used in stem cell therapy, the therapeutic effect thereof will be enhanced. The ligustilide-comprising composition can be ligustilide itself, or can include ligustilide and a solvent, wherein ligustilide is dissolved into the solvent. For example, ligustilide may be added into the culture medium which corresponds to the stem cell that is to be treated to provide the composition of the present invention, the composition is then used for treating stem cells. In another example, ligustilide may be added into a solvent, such as DMSO or ethanol, to provide a composition of the present invention, the composition is then used for treating stem cells. Alternatively, when the composition is ligustilide itself, the composition can be directly added into the culture medium which contains the stem cell that is to be treated to perform a pre-treatment. With a provision, to maintain the activity of the stem cells, the pre-treating method of the present invention shall be conducted in a culture medium of the stem cells. Therefore, if the composition for treating the stem cells of the present invention does not comprise a culture medium of the stem cells, the stem cells that are to be treated should be placed in a culture medium of the stem cells to conduct the pre-treatment.

Any suitable culturing conditions can be chosen and used depending on the type of stem cell. In general, the amount of ligustilide may range from about 0.1 μg to about 40 μg, preferably from about 0.1 μg to about 20 μg, and most preferably from about 0.1 μg to about 10 μg per milliliter of the culture medium for stem cells. For instance, as illustrated in the examples provided hereinafter, when ligustilide is used in the pre-treatment of ADSCs, the amount of ligustilide preferably ranges from about 0.5 μg to about 5 μg per milliliter of the culture medium for stem cells, this amount can effectively increase the expression of differentiation-promoting genes in the ADSCs, increase the expression of homing-promoting genes in the ADSCs, and decrease the expression of inflammatory genes in the ADSCs.

Any suitable culture medium of stem cells can be used in the present invention, as long as the culture medium corresponds to the stem cells that are to be treated. The components of the culture medium of stem cells may be adjusted depending on the types of the stem cells that are to be treated. In general, a culture medium of stem cells comprises a base culture medium, an animal serum (e.g., fetal bovine serum), non-essential amino acids (NEAA) and L-glutamine, etc. Examples of the base medium suitable for the method of the present invention include, but are not limited to, K-SFM (keratinocyte-Serum Free Medium), DMEM (Dulbecco's Modified Eagle's Medium), MEM (Minimum Essential Medium), α-MEM (α-Minimum Essential Medium), BME (Basal Media Eagle), MEM/F12 medium, Ham's F10 medium, Ham's F12 medium, and RPMI (Rosewell Park Memorial Institute). For instance, when the method of the present invention is used for enhancing the therapeutic effect of ADSCs, K-SFM may be used as the base medium to conduct pre-treatment.

Accordingly, the present invention also provides a stem cell kit with an enhanced therapeutic effect of the stem cell, comprising (1) a stem cell; (2) a culture medium for the stem cell; and (3) ligustilide. The selection of the stem cells and culture medium, as well as the condition and method of using ligustilide are all in line with the above descriptions.

Usually, the components (1), (2) and (3) of the kit of the present invention are packaged and stored separately, and could be transported, sold separately or in a set. Component (1), (2) and (3) is combined with each other at the customer's facility prior to being used according to the preset culture procedure and processes.

The inventors of the present invention also found that when ligustilide is used in combination with ligustilide-treated stem cells in a stem cell therapy, a preferable therapeutic effect can be provided. Therefore, the kit of the present invention may comprise a first part of ligustilide and a second part of ligustilide, wherein the first part is used in combination with the culture medium to pre-treat the stem cells, and the second part is used in combination with the ligustilide-treated stem cells in a stem cell therapy.

Therefore, the present invention also relates to a use of ligustilide in the manufacture of a medicament, wherein the medicament is used in combination with a ligustilide-treated stem cell. The selection of stem cells, as well as the condition and method of using ligustilide are all in line with the above descriptions.

The medicament provided by the present invention can be used in combination with ligustilide-treated stem cells for at least one of the following: treating autoimmune diseases (e.g., diabetes mellitus and autoimmune rejection), treating digestive diseases (e.g., anus/digestive fistula diseases), treating hepatic diseases (e.g., hepatocirrhosis and hepatic fibrosis), treating renal diseases (e.g., renal failure), treating cardiovascular diseases (e.g., stroke and myocardial infarction), treating neurological diseases (e.g., Alzheimer's disease and Parkinson's disease), treating hematological diseases (e.g., leukemia), treating bone degeneration (e.g., degenerative arthritis, degeneration of knee cartilage), treating periodontitis, treating tendonitis, treating spinal injury, treating head trauma, plastic surgery (e.g., hemifacial atrophy and sunken scar), treating alopecia, whitening skin and eliminating wrinkles. In one embodiment of the present invention, the medicament is used in combination with ligustilide-treated stem cells for treating strokes.

The medicament provided by the present invention can be manufactured into any form, and can be administered in any suitable form. For example, the medicament can be administered by oral, subcutaneous, nasal or intravenous to a subject in need, but is not limited thereby. Depending on the form and purpose, the medicament can further comprise a pharmaceutically acceptable carrier.

For oral administration, the medicament manufactured by the present invention can comprise a pharmaceutically acceptable carrier that would not adversely affect the desired activity of ligustilide. Examples of the carrier include solvents (e.g., water, saline, dextrose, glycerol, ethanol or its analogs, or a combination thereof), oily solvents, diluents, stabilizers, absorption retarders, disintegrants, emulsifiers, antioxidants, adhesives, lubricants, moisture absorbents, solid carriers (e.g., starch and bentonite). The medicament can be provided in any suitable form for oral administration, such as a tablet, a capsule, a granule, a powder, a fluid extract, a solution, syrup, a suspension, an emulsion, a tincture, etc.

For subcutaneous or intravenous administration, the medicament manufactured by using ligustilide of the present invention can comprise one or more component(s), such as an isotonic solution, a saline buffer solution (e.g., a phosphate buffer solution or a citrate buffer solution), a solubilizer, an emulsifier, 5% sugar solution, and other carriers, etc., to provide the medicament as an intravenous injection, an emulsion intravenous injection, a powder injection, a suspension injection, or a powder-suspension injection. Alternatively, the medicament can be prepared as a pre-injection solid. The pre-injection solid can be provided as a form which may dissolve into, suspend in other solutions, or be emulsified. In addition, prior to the administration into a subject in need, the pre-injection solid can be dissolved into, suspended in other solutions, or be emulsified, to provide a desired injection form.

Optionally, the medicament manufactured by using ligustilide of the present invention may comprise other flavoring agents, toner, or coloring agents to enhance the taste and visual appeal of the resultant medicament. A suitable amount of a preservative, a conservative, an anti-septic, an anti-fungus reagent, and etc., may also be added to improve the storability of the resultant medicament. In addition, the medicament may further comprise one or more active components or be used in combination with a medicament comprising one or more other active components to further enhance the effects of the medicament or to increase the application flexibility and adaptability of the formulation thus provided, as long as the other active components have no adverse effect on the desired effect of ligustilide.

Depending on the requirements of the subject, the medicament manufactured by using ligustilide of the present invention, can be applied with various administration frequencies, such as once a day, several times a day or once every few days, etc. For example, when the medicament manufactured by using ligustilide of the present invention is used in combination with the ligustilide-treated stem cells for treating a stroke in a human body, the dosage of the medicament is about 1 mg (as ligustilide)/kg-body weight to about 120 mg (as ligustilide)/kg-body weight per day, preferably about 10 mg (as ligustilide)/kg-body weight to about 95 mg (as ligustilide)/kg-body weight per day, and more preferably about 20 mg (as ligustilide)/kg-body weight to about 40 mg (as ligustilide)/kg-body weight per day, wherein the unit "mg/kg-body weight" means the dosage required per kg-body weight of the treated subject. However, for patients with acute conditions, the dosage can be increased to several times or several tens of times, depending on the practical requirements. In one embodiment of the present invention, ligustilide is used in the use of manufacturing medicament, wherein the medicament is used in combination with the ligustilide-treated stem cells and the dosage of the medicament is about 30 mg (as ligustilide)/kg-body weight or about 90 mg (as ligustilide)/kg-body weight.

The present invention also relates a method of stem cell treatment, comprising administering ligustilide-treated stem cells to a subject in need. In addition, the method may optionally comprise administering additional ligustilide and ligustilide-treated stem cells, either simultaneously or separately, to a subject in need. The treatment of stem cells, selection of materials, dosage of ligustilide for administration, and the application of relative therapy are all in line with the above descriptions.

The present invention will be further illustrated in detail with specific examples as follows. However, the following examples are provided only for illustrating the present invention, and the scope of the present invention is not limited thereby.

EXAMPLES

A. Cellular Experiments

Example 1

Examination of Cell Survival Rate (MTT Assay)

Adipose stem cells (ADSCs) were cultured in keratinocyte-serum free medium (K-SFM; Gibco) at 37° C. in 5% $CO_2$. The K-SFM was added with bovine pituitary extract (Gibco), recombinant epidermal growth factor (Gibco), N-acetyl-L cysteine (with a final concentration of $2\times10^{-3}$ M; Sigma), L-ascorbic acid 2-phosphate sesquimagnesium salt hydrate with a (final concentration of $2\times10^{-4}$ M; Sigma), and 10% of fetal bovine serum (FBS; Hyclone).

Figure 1B:
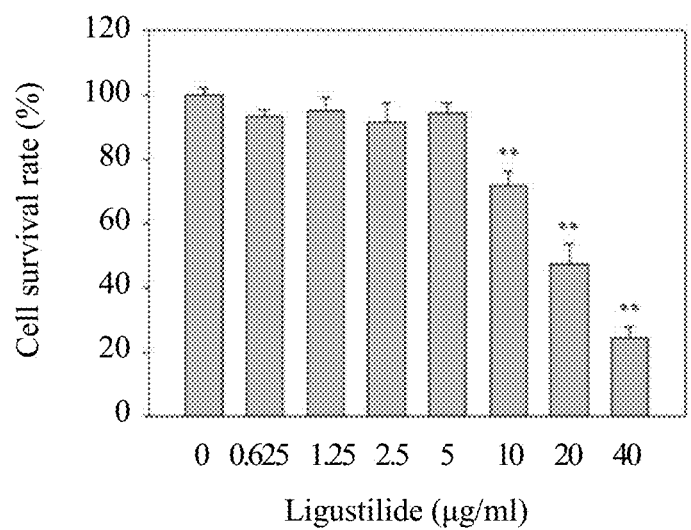

The above ADSCs-containing culture medium was divided into A and B groups. Each group has 8 sub-groups. Different concentrations (0, 0.625, 1.25, 2.5, 5, 10, 20 and 40 μg/ml) of (Z)-ligustilide were added into each sub-groups to conduct a treatment for 24 hours in group A, and 48 hours in group B. Then, 3-(4,5-dimethylthiazol-2-yl)-2,5-diphenyltetrazolium bromide (MTT) analytic reagent was used to stain the cells, and the absorbance at a wavelength of 570/630 nm ($OD_{570-630}$) of the samples were measured by a visible spectrometer and the data were calculated to understand whether ligustilide will affect the survival rate of ADSCs. The results of group A and B are shown in FIGS. 1A and 1B.

Example 2

The Effects of Ligustilide on Increasing the Expression of Differentiation-Promoting Genes, Increasing the Expression of Homing-Promoting Genes, and Decreasing the Expression of Inflammatory Genes Experiment (1)

Treat Stem Cells with Ligustilide

ADSCs were cultured in the K-SFM as prepared in Example 1 at 37° C. in 5% $CO_2$. The ADSCs were divided into 5 groups, and each group was treated with different concentrations (0, 0.625, 1.25, 2.5, 5 and 10 μg/ml) of (Z)-ligustilide for 24 hours, respectively.

Experiment (2)

Preparation of Total RNA of the Stem Cells

The culture medium were removed from each group of stem cells in Experiment (1), then 1 ml of TRIzol reagent (Invitrogen) was added into each well and incubated at room temperature for 5 minutes. The stem cells were scraped by using a spatula and placed into a 1.5 ml microtube. Then, the cells were lysed completely, and 0.2 ml of trichloromethane ($CHCl_3$) was added into the microtube. The microtube was shaken up and down for 15 seconds and incubated at room temperature for 2 to 3 minutes. The mixture was centrifuged (at 12000 g for 15 minutes at 4° C.). The supernatant was transferred into another 1.5 ml microtube, and 0.5 ml of isopropanol was added therein and mixed completely. The mixture was incubated at room temperature for 10 minutes and then centrifuged (at 12000 g for 10 minutes at 4° C.). The supernatant was removed. The remained sediment was washed with 1 ml of 75% ethanol-containing DEPC water (i.e. diethylpyrocarbonate-treated $H_2O$) and centrifuged (7500 g at 4° C. for 5 minutes) again. The supernatant was removed. The remained sediment was dried by vacuum-pumping. The dried sediment was dissolved in about 0.01 ml to 0.02 ml of DEPC water to obtain total RNA of ADSCs of experimental group and blank group, respectively. The absorbance at a wavelength of 260 nm ($OD_{260}$) of the samples were determined by a spectrophotometer (DU-800, Beckman) to evaluate the concentration of RNA. Then, the RNA was stored at −80° C. and used in the following Experiment (3).

Experiment (3)

Reverse Transcription Polymerase Chain Reaction (RT-PCR) and Gel Electrophoresis The effects of ligustilide on increasing the expression of differentiation-promoting genes (e.g., BDNF and NURR1), increasing the expression of homing-promoting genes (e.g., CXCR4 and SDF1αβ), and decreasing the expression of inflammatory genes (e.g., IL-6 and IL-8) was analyzed by reverse transcription polymerase chain reaction (RT-PCR), wherein the gene expression of glyceraldehyde 3-phosphate dehydrogenase (GAPDH) was served as a control group, and the steps were described as follows.

The total RNA provided in the above Experiment (2) was reverse transcribed into cDNA. 2.5 μl of each primer (10 pM) shown in Table 1A, 7.5 μl of dd$H_2O$, and 12.5 μl of EconoTaq® PLUS GREEN 2X Master Mix (Lucigen, Middleton, Wis., USA) were mixed with 2.5 μl of the cDNA. The mixture was placed in a RT-PCR machine. The reaction conditions were set as follows: i) 94° C. for 30 seconds, 55° C. for 30 seconds, and 94° C. for 60 seconds, with 30 cycles of the aforesaid steps; ii) 72° C. for 10 minutes; and iii) cooling to 4° C. to stop the reaction.

Figure 2:
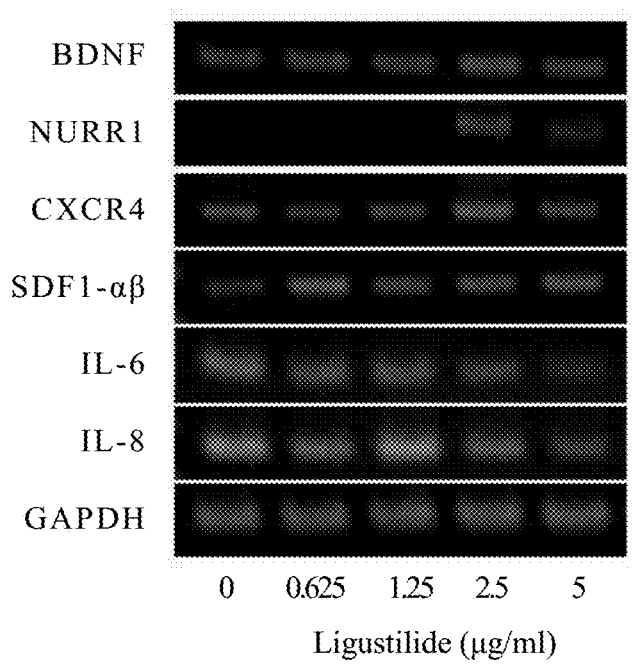
FIG. 2 is a photograph showing the expression of different genes in stem cells which have been treated with different concentration of ligustilide and analyzed by RT-PCR, wherein such genes include differentiation-promoting genes (i.e., BDNF and NURR1), homing-promoting genes (i.e., CXCR4 and SDF1αβ) and inflammatory genes (i.e., IL-6 and IL-8)

The obtained RT-PCR product was analyzed by 1.5% agarose gel electrophoresis for 30 minutes (voltage: 100 volts (V)). Then, the gel was placed in and stained with ethidium bromide (EtBr) for 10 minutes, and photographed by a gel image documentation system (DOC PRINT DP-001FDC, VilberLourmat France). The results are shown in FIG. 2. The expression levels of the genes were quantified by a software, Image J. The results are shown in Table 1B.

TABLE 1A

| Name | Nucleotide sequence of primer | SEQ ID NO. |
|---|---|---|
| BDNF | Forward: 5'-GAGCTGAGCGTGTGTGACAG-3' | 1 |
|  | Reverse: 5'-ACTGGGTAGTTCGGCACTGG-3' | 2 |
| NURR1 | Forward: 5'-CGCACATGATCGAGCAGAGG-3' | 3 |
|  | Reverse: 5'-ATTCCGGCGACGCTTGTCCA-3' | 4 |
| CXCR4 | Forward: 5'-GGCCTTCATCAGTCTGGACC-3' | 5 |
|  | Reverse: 5'-AGTAAGGCAGCCAACAGGCG-3' | 6 |
| SDF1αβ | Forward: 5'-ATGAACGCCAAGGTCGTGGTC-3' | 7 |
|  | Reverse: 5'-CTTGTTTAAAGCTTTCTCCAGGTACT-3' | 8 |
| IL-6 | Forward: 5'-TGCCAGCCTGCTGACGAAGC-3' | 9 |
|  | Reverse: 5'-TCTGTGCCCAGTGGACAGGT-3' | 10 |
| IL-8 | Forward: 5'-GCTGGCCGTGGCTCTCTTGG-3' | 11 |
|  | Reverse: 5'-TCCACAACCCTCTGCACCCA-3' | 12 |
| GAPDH | Forward: 5'-GGAGCCAAACGGGTCATCATCTC-3' | 13 |
|  | Reverse: 5'-GAGGGGCCATCCACAGTCTTCT-3' | 14 |

TABLE 1B

|  | 0 μg/ml | 0.625 μg/ml | 1.25 μg/ml | 2.5 μg/ml | 5 μg/ml |
|---|---|---|---|---|---|
| BDNF | 4851.77 | 5411.77 | 4915.77 | 7069.72 | 5083.65 |
| NURR1 | 0.00 | 0.00 | 0.00 | 6694.43 | 3360.55 |
| CXCR4 | 4136.94 | 2744.11 | 3719.23 | 6539.03 | 4138.77 |
| SDF1αβ | 2482.23 | 6766.31 | 4065.23 | 4791.36 | 5767.31 |
| IL-6 | 13621.92 | 7756.00 | 8204.13 | 5629.93 | 2804.03 |
| IL-8 | 9302.18 | 6102.10 | 9691.71 | 5840.23 | 3487.33 |
| GAPDH | 7179.84 | 6892.26 | 7615.03 | 8186.79 | 8265.67 |

As shown in FIG. 2 and Table 1B, as compared to the control group (i.e., GAPDH), the gene expression levels of NURR1, BDNF, CXCR4 and SDF1αβ were increased because of the treatment of ligustilide, while the gene expression levels of IL-6 and IL-8 were decreased because of the treatment of ligustilide. The results indicate that ligustilide can effectively increase the expression of differentiation-promoting genes, increase the expression of homing-promoting genes, and decrease the expression of inflammatory genes, thereby decreasing inflammatory reaction in stem cells and increasing the survival rate of stem cells.

B. Animal Experiments

Example 3

Establishment of the Stroke Mouse Model

To avoid the influence of oppression and anxiety that is caused by not adapting to the caging environment on the procedures and results of the experiments, male BALB/c mice were given several days to adapt to the environment after being separated into individual cages, and analyzed by a neurobehavioral study one day before being induced to form thrombus in their middle cerebral artery (MCA) by thrombin.

Before the surgery, each male BALB/c mouse (8-week-old and weight 25 g) was anesthetized with 0.25 ml of 4% chloral hydrate. During the surgery, isoflurane was used consistently to keep the mice anesthetized to prevent the mice from becoming conscious during the surgery and affecting the experimental results.

After anesthetization, a mouse were positioned in a stereotaxic head frame. The skin 1 mm posterior to the right orbit of the mouse was biopsied to expose the connective tissue and muscle. The biopsied skin and muscle were lifted and fixed bilaterally. Then, a miniature electric drill was used to conduct open-skull surgery on the mouse. First, a circular area of skull was biopsied from the top of the malar bone of the mouse. Then, a microscope was used to find the middle cerebral artery, and a Laser Doppler Flowmetry probe was set at 1 mm from the top of the middle cerebral artery to detect the blood flow of mouse before thrombin injection and after thrombin injection. The glass probe set on a microinjector was used to suck up 1 μl of thrombin, and then the microinjector was placed on a hydraulic 3-way regulating instrument and moved to gradually approach the middle cerebral artery. After the glass probe passes through the meninges and inserts into the blood vessel, thrombin was immediately injected into the middle cerebral artery by a pneumatic pump. After 10 minutes, the glass probe was gradually removed and a stroke mouse model was obtained, hereinafter referred to as "stroke group" (injected with thrombin). Additionally, a group that was not treated with thrombin injection was used as a "pseudo-operation group."

Example 4

Treating the Stroke Mouse with Stem Cell Therapy

ADSCs were cultured in K-SFM at 37° C. in 5% $CO_2$ and pre-treated with 2.5 μg/ml of ligustilide for 24 hours to obtain "ligustilide-treated stem cells". In addition, ADSCs without ligustilide pre-treatment was referred to as "untreated stem cells." Before being injected into the mouse brain, both the aforesaid stem cells were stained with Hoechst dye for 1 hour for follow-up tracking.

Within 2 hours post-surgery, the aforesaid "ligustilide-treated stem cells" were injected into three sites of the brain of the "stroke group" mouse provided in Example 3 (each mouse was injected with a total amount of $1\times10^6$ cells of the "ligustilide-treated stem cells"), thus a "stroke+ligustilide-treated stem cells group" was obtained, wherein the injection sites can be seen in, for example, "Enhancement of neuroplasticity through upregulation of beta1-integrin in human umbilical cord-derived stromal cell implanted stroke model. *Neurobiol Dis.* 27(3):339-353 (2007)," which is entirely incorporated hereinto by reference. In addition, a "stroke+untreated stem cells group" would be obtained from the "stroke group" mouse injected with the "untreated stem cells," while the control group was "stroke group" mouse injected with equal value of saline, hereinafter referred to as "stroke+saline group."

Example 5

Ligustilide Enhances the Therapeutic Effect of Stem Cells

The "Pseudo-operation group (i.e., Group 1)" mouse provided in Example 3, "stroke+saline group (i.e., Group 2)" mouse provided in Example 4, "stroke+untreated stem cells group (i.e., Group 3)" mouse provided in Example 4, and "stroke+ligustilide-treated stem cells group (i.e., Group 4)" mouse provided in Example 4 were analyzed by a neurobehavioral tests one day before conducting the therapy and 1, 3, 7, 14 days post-therapy, respectively. The neurobehavioral tests includes Rotarod Analysis and Beam Walking Analysis.

Figure 3:
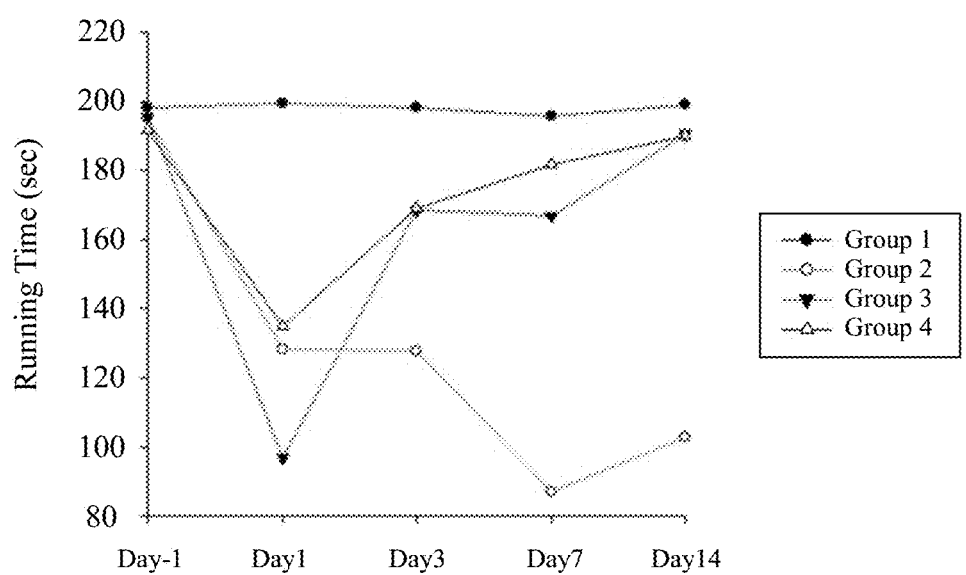
FIG. 3 is a curve diagram showing the coordination of mice which have been treated with different conditions and analyzed by Rotarod Analysis, wherein the horizontal axis represents the time post-treatment and the vertical axis represents the running time of the mice; wherein Group 1 is a non-stroke mouse without treatment (i.e., a pseudo-operation group), Group 2 is a stroke mouse administered with saline, Group 3 is a stroke mouse administered with stem cells without being treated with ligustilide, and Group 4 is a stroke mouse administered with ligustilide-treated stem cells.

In Rotarod Analysis, the running time of the mouse on the roller was used to evaluate the coordination of mouse. The results are shown in FIG. 3. A longer running time of the mouse represents a better coordination. In Beam Walking Analysis, the mouse was placed on a balance beam. The time required for mouse to pass through the balance beam and number of foot-faults (i.e., foot-fault score) were recorded to reflect the balance ability of the mouse. The results are shown in FIGS. 4A and 4B.

As shown in FIG. 3, the running time of "stroke+ligustilide-treated stem cells group" mouse on the roller was significantly more than that of the "stroke+untreated stem cells group" mouse. This result indicates that the "stroke+ligustilide-treated stem cells group" mouse has better coordination than that of the "stroke+untreated stem cells group" mouse.

Figure 4A:
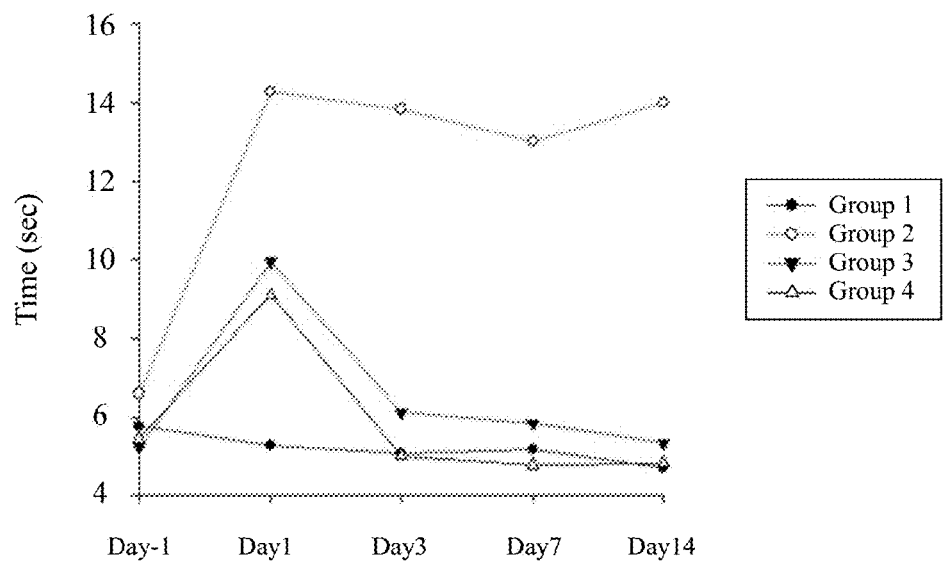
FIGS. 4A and 4B are curve diagrams showing the balance ability of mice which have been treated with different conditions and analyzed by Beam Walking Analysis.
Figure 4B:
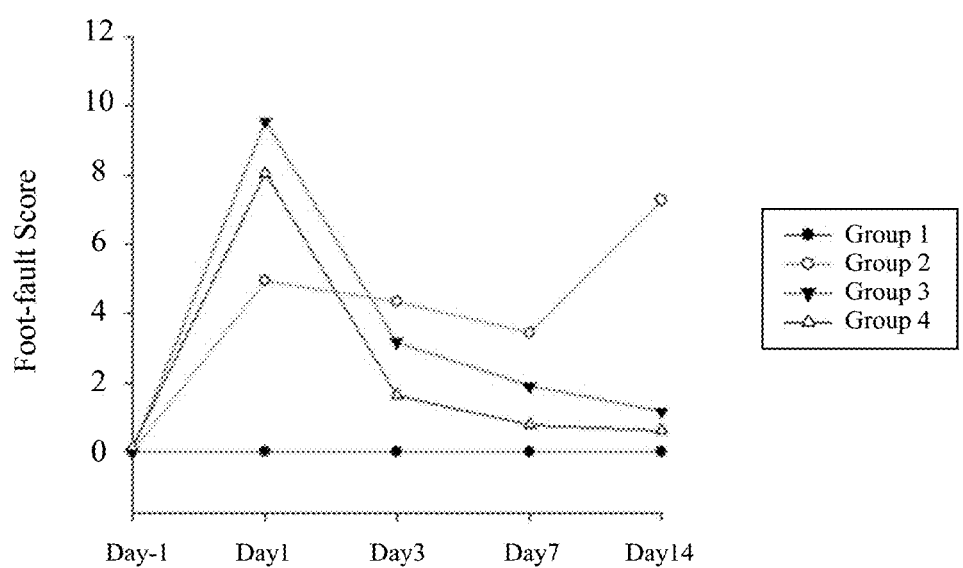

As shown in FIG. 4A, the "stroke+ligustilide-treated stem cells group" mouse requires less time to pass balance beam than that of the "stroke+untreated stem cells group" mouse. The time required for the mouse 3 days post-therapy of ligustilide-treated stem cells to pass the balance beam was shortened significantly. In addition, as shown in FIG. 4B, the foot-fault score of the "stroke+ligustilide-treated stem cells group" mouse was significantly lower than that of the "stroke+untreated stem cells group" mouse. The aforesaid results indicate that the mouse treated with ligustilide-treated stem cells has a better balance ability and the balance ability was recovered significantly in 3 days post-therapy.

The above results indicate that ligustilide actually has an effect of enhancing the therapeutic effect of stem cells.

Example 6

Figure 5A:
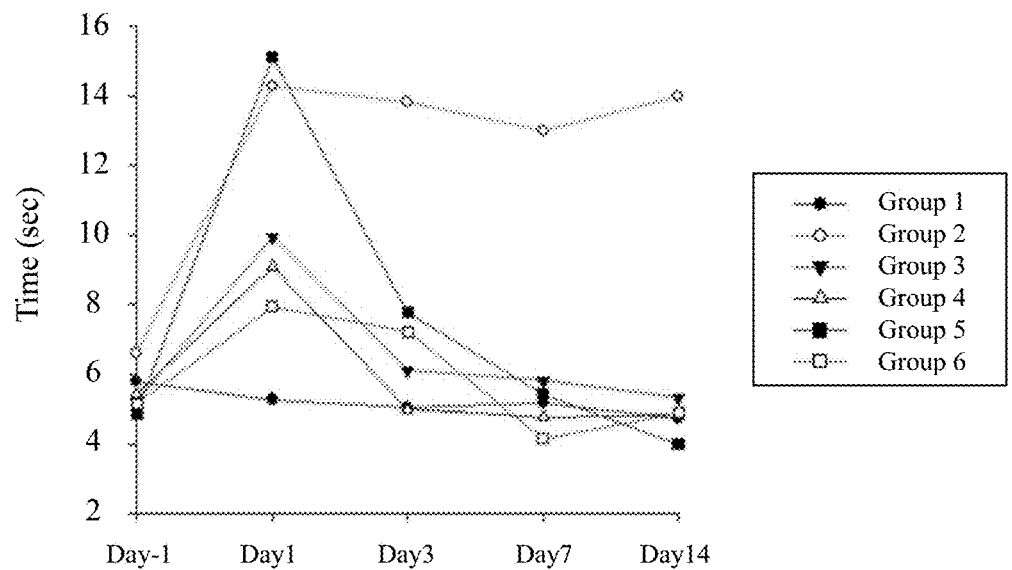
FIGS. 5A and 5B are curve diagrams showing the balance ability of mice which have been treated in different conditions and analyzed by Beam Walking Analysis.
Figure 5B:
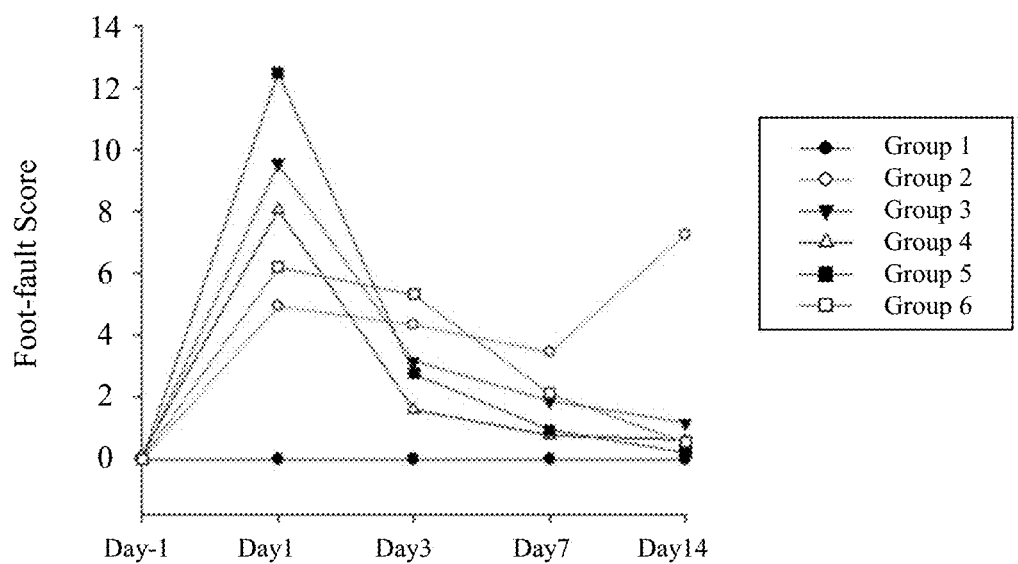
Figure 6A:
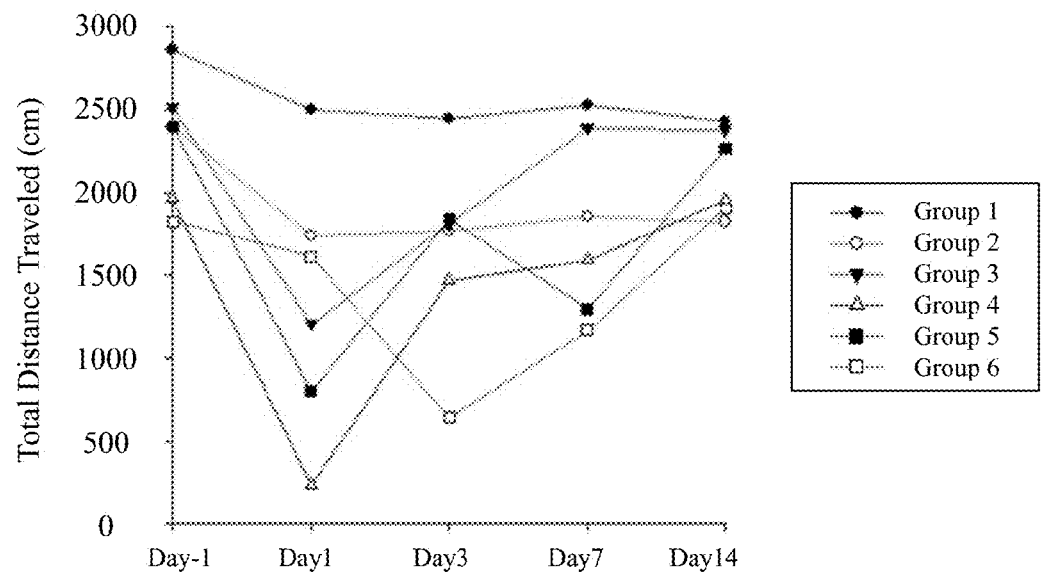
FIGS. 6A and 6B are curve diagrams showing the motor ability of mice which have been treated with different conditions and analyzed by Locomotor Activity Box Test.
Figure 6B:
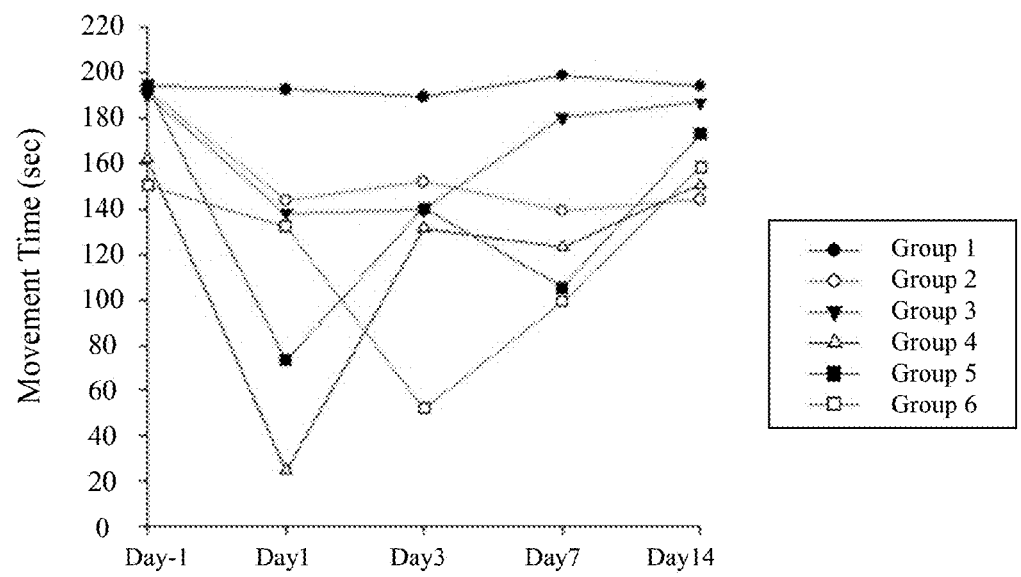

Use a Combination of Ligustilide and Ligustilide-Treated Stem Cells to Treat Diseases In addition to "pseudo-operation group (i.e., Group 1)," "stroke+saline group (i.e., Group 2)," "stroke+untreated stem cells group (i.e., Group 3)," and "stroke+ligustilide-treated stem cells group (i.e., Group 4)," (Z)-ligustilide (30 mg/kg-body weight or 90 mg/kg-body weight) and "ligustilide-treated stem cells" provided in Example 4 were used in combination to inject into the brain of a stroke mouse, which referred to as "stroke+ligustilide-treated stem cells+ligustilide (30 mg/kg-body weight) group (i.e., Group 5)" and "stroke+ligustilide-treated stem cells+ligustilide (90 mg/kg-body weight) group (i.e., Group 6)," respectively. The aforesaid six groups were analyzed by Beam Walking Analysis and Locomotor Activity Box Test one day before conducting the therapy and 1, 3, 7, 14 days post-therapy, respectively. The results of Beam Walking Analysis are shown in FIGS. 5A and 5B, and the results of Locomotor Activity Box Test are shown in FIGS. 6A and 6B. Locomotor Activity Box Test was conducted through a computer-connecting sensor to display and record the movement data of mouse in the Locomotor activity box. The movement data, that includes horizontal displacement (e.g., walking), vertical displacement (e.g., head-up and climbing) and total distance traveled, were recorded and analyzed statistically to show the motor ability of the mouse.

As shown in FIGS. 5A and 5B, as compared to the "stroke+ligustilide-treated stem cells group" mouse, the time required for "stroke+ligustilide-treated stem cells+ligustilide (30 mg/kg-body weight) group" mouse and "stroke+ligustilide-treated stem cells+ligustilide (90 mg/kg-body weight) group" mouse to pass the balance beam were shorter significantly, and the foot-fault score were also reduced significantly, wherein the "stroke+ligustilide-treated stem cells+ligustilide (30 mg/kg-body weight) group" mouse has the most obvious efficiency thereof. The aforesaid results indicate that the stroke mouse treated with "ligustilide" and "ligustilide-treated stem cells" in combination has a better balance ability. In particular, the balance ability of the stroke mouse treated with "30 mg/kg-body weight of ligustilide" and "ligustilide-treated stem cells" in combination was recovered most significantly.

As shown in FIGS. 6A and 6B, the total distance traveled and movement time of the "stroke+ligustilide-treated stem cells+ligustilide (30 mg/kg-body weight) group" mouse and the "stroke+ligustilide-treated stem cells+ligustilide (90 mg/kg-body weight) group" mouse in the Locomotor activity box were all significantly longer than that of the "stroke+ligustilide-treated stem cells group" mouse, wherein the "stroke+ligustilide-treated stem cells+ligustilide (30 mg/kg-body weight) group" mouse has the most obvious efficiency thereof. The aforesaid results indicate that the stroke mouse treated with "ligustilide" and "ligustilide-treated stem cells" in combination has a better motor ability. In particular, the motor ability of the stroke mouse treated with "30 mg/kg-body weight of ligustilide" and "ligustilide-treated stem cells" in combination was recovered most significantly.

The above results indicate that a combination of "ligustilide" and "ligustilide-treated stem cells" can actually further enhance the therapeutic effect of stem cells.

The above examples are used to illustrate the principle and efficacy of the present invention but not used to limit to the present invention. People skilled in this field may proceed with a variety of modifications and replacements based on the disclosures and suggestions of the invention as described without departing from the technical principle and spirit thereof. Therefore, the scope of protection of the present invention is that as defined in the claims as appended.

What is claimed is:

1. A method for enhancing the therapeutic effect of stem cells on autoimmune diseases, cardiovascular diseases, and/or hematological diseases, comprising:
   a) pre-treating the stem cells by culturing the stem cells in a culture medium comprising 0.1 μg/ml to 20 μg/ml of ligustilide to increase the expression of differentiation-promoting genes in the stem cells, increase the expression of homing-promoting genes in the stem cells, and/or decrease the expression of inflammatory genes in the stem cells, wherein the culture medium does not comprise insulin; and
   b) administering an effective amount of stem cells pre-treated in step a) to a subject suffering from autoimmune diseases, cardiovascular diseases and/or hematological diseases.

2. The method of claim 1, wherein the stem cell is an embryonic stem cell, an adult stem cell, or an induced pluripotent stem cell.

3. The method of claim 2, wherein the stem cells are adipose-derived stem cells.

4. The method of claim 1, wherein the culture medium comprises 0.1 μg/ml to 10 μg/ml of ligustilide.

5. The method of claim 4, wherein the culture medium comprises 0.5 μg/ml to 5 μg/ml of ligustilide.

6. The method of claim 1, wherein the method is used for enhancing the therapeutic effect of stem cells on cardiovascular diseases, comprising:
   a) pre-treating the stem cells by culturing the stem cells in a culture medium comprising 0.1 μg/ml to 20 μg/ml of ligustilide to increase the expression of differentiation-promoting genes in the stem cells, increase the expression of homing-promoting genes in the stem cells, and/or decrease the expression of inflammatory genes in the stem cells, and the culture medium does not comprise insulin; and
   b) administering an effective amount of stem cells pre-treated in step a) to a subject suffering from cardiovascular diseases.

7. The method of claim 6, wherein the stem cell is an embryonic stem cell, an adult stem cell, or an induced pluripotent stem cell.

8. The method of claim 7, wherein the stem cells are adipose-derived stem cells.

9. The method of claim 6, wherein the cardiovascular disease is stroke.

10. The method of claim 6, wherein the culture medium comprises 0.1 μg/ml to 10 μg/ml of ligustilide.

11. The method of claim 10, wherein the culture medium comprises 0.5 μg/ml to 5 μg/ml of ligustilide.

12. The method of claim 1, wherein the method is used for enhancing the therapeutic effect of stem cells on hematological diseases, comprising:
   a) pre-treating the stem cells by culturing the stem cells in a culture medium comprising 0.1 μg/ml to 20 μg/ml of ligustilide to increase the expression of differentiation-promoting genes in the stem cells, increase the expression of homing-promoting genes in the stem cells, and/or decrease the expression of inflammatory genes in the stem cells, and the culture medium does not comprise insulin; and
   b) administering an effective amount of stem cells pre-treated in step a) to a subject suffering from hematological diseases.

13. The method of claim 12, wherein the stem cell is an embryonic stem cell, an adult stem cell, or an induced pluripotent stem cell.

14. The method of claim 13, wherein the stem cells are adipose-derived stem cells.

15. The method of claim 12, wherein the culture medium comprises 0.1 μg/ml to 10 μg/ml of ligustilide.

16. The method of claim 15 wherein the culture medium comprises 0.5 µg/ml to 5 µg/ml of ligustilide.

* * * * *